US012766049B2

(12) United States Patent
Cannon

(10) Patent No.: US 12,766,049 B2
(45) Date of Patent: Oct. 20, 2026

(54) REUSABLE SWIM DIAPER

(71) Applicant: O2COOL, LLC, Chicago, IL (US)

(72) Inventor: Becky Cannon, Ashville, NC (US)

(73) Assignee: O2COOL, LLC, Chicago, IL (US)

( * ) Notice: Subject to any disclaimer, the term of this patent is extended or adjusted under 35 U.S.C. 154(b) by 316 days.

(21) Appl. No.: 18/357,853

(22) Filed: Jul. 24, 2023

(65) Prior Publication Data

US 2024/0252366 A1 Aug. 1, 2024

Related U.S. Application Data

(60) Provisional application No. 63/482,387, filed on Jan. 31, 2023.

(51) Int. Cl.

| | |
|---|---|
| ***A61F 13/49*** | (2006.01) |
| ***A41D 7/00*** | (2006.01) |
| ***A41D 31/10*** | (2019.01) |
| ***A61F 13/15*** | (2006.01) |
| ***A61F 13/494*** | (2006.01) |
| ***A61F 13/496*** | (2006.01) |

(52) U.S. Cl.

CPC ........ *A61F 13/49014* (2013.01); *A41D 7/005* (2013.01); *A41D 31/10* (2019.02); *A61F 13/49006* (2013.01); *A61F 13/49011* (2013.01); *A61F 13/4963* (2013.01); *A41D 2500/10* (2013.01); *A61F 2013/15195* (2013.01); *A61F 2013/49093* (2013.01); *A61F 2013/49433* (2013.01); *A61F 2013/4944* (2013.01)

(58) Field of Classification Search

CPC .................... A41D 31/10; A41D 7/005; A61F 2013/15195; A61F 2013/49093; A61F 13/49006; A61F 13/49011; A61F 13/496; A61F 13/49004; A61F 2013/4944

See application file for complete search history.

(56) References Cited

U.S. PATENT DOCUMENTS

| | | | | |
|---|---|---|---|---|
| 4,846,825 | A | 7/1989 | Enloe et al. | |
| 5,209,743 | A | 5/1993 | Hardison | |
| 6,996,851 | B2 * | 2/2006 | Nordness | A41D 7/005 2/919 |
| 7,678,094 | B1 | 3/2010 | Cannon et al. | |
| 11,154,431 | B1 * | 10/2021 | Yip | A61F 13/15747 |
| 2003/0181885 | A1 | 9/2003 | Harkness | |
| 2006/0070163 | A1 | 4/2006 | Beck et al. | |

(Continued)

FOREIGN PATENT DOCUMENTS

| | | | |
|---|---|---|---|
| WO | 2008146289 | A2 | 12/2008 |
| WO | 2022246494 | A1 | 12/2022 |

OTHER PUBLICATIONS

Prosecution History for U.S. Appl. No. 18/189,313, filed Mar. 24, 2023.

*Primary Examiner* — Michele Kidwell
(74) *Attorney, Agent, or Firm* — Thompson Coburn LLP

(57) ABSTRACT

A reusable swim diaper having a main body made of waterproof coated (bonded polyurethane) polyester configured with an elasticized waist opening and elasticized leg openings, the main body having improved degradation from laundering and is suitable for multiple launderings and reuse without degrade and having gussets formed at and extending from the leg openings to minimize the flow of particulate matter, such as fecal matter, between the inside and the outside of the swim diaper.

10 Claims, 4 Drawing Sheets

(56) References Cited

U.S. PATENT DOCUMENTS

| | | | |
|---|---|---|---|
| 2009/0216209 | A1 | 8/2009 | Ekstrom |
| 2015/0257944 | A1 | 9/2015 | Cannon et al. |
| 2019/0209394 | A1 | 7/2019 | Lässig |
| 2022/0079251 | A1 | 3/2022 | Calamia |
| 2024/0252366 | A1 | 8/2024 | Cannon |

* cited by examiner

REUSABLE SWIM DIAPER

REFERENCE TO RELATED APPLICATIONS

This application claims the benefit of Provisional Application No. 63/482,387, filed Jan. 31, 2023, entitled "REUSABLE SWIM DIAPER." The benefit under 35 USC § 119(e) of the United States provisional application is hereby claimed, and the aforementioned application is hereby incorporated herein by reference in its entirety.

STATEMENT REGARDING FEDERALLY SPONSORED RESEARCH OR DEVELOPMENT

Not applicable.

COPYRIGHT NOTICE

A portion of this disclosure contains material which is subject to copyright protection. The copyright owner has no objection to the photocopy reproduction by anyone of the patent document or the patent disclosure in exactly the form it appears in the Patent and Trademark Office patent file or records, but otherwise reserves all copyright rights whatsoever. 37 C.F.R 1.71(d).

BACKGROUND OF THE INVENTIVE CONCEPT

1. Field of the Invention

The present inventive concept relates to reusable swim diapers to provide a snug fit. More particularly, but not exclusively, this inventive concept relates to reusable swim diapers including specifically designed gussets with an elastic and enhanced material configured to provide a snug fit and to prevent leakage accidents of human waste in pools or other bathing facilities.

DESCRIPTION OF THE RELATED ART

Diapers have been used to soak up accidents caused by infants, young children and even elderly people. These diapers are generally formed to include insertion holes for the legs of a user (i.e., infants, young children and elderly people) to insert therethrough and a waistband that can be secured around a user's waist. Such diapers are designed to catch human waste, including feces. However, the insertion holes formed for the legs to fit through generally cannot be designed to sufficiently fit around a user's legs to prevent gaps from forming between the legs and the diaper insertion holes, thus allowing some amount of human waste, including to escape from the diaper and leak out from between a user's leg and the leg insertion hole. This problem is specifically detrimental when an infant, young child or an elderly person is wearing the diaper in a swimming pool where such waste leakage into the swimming pool most likely can result in the need to close the pool and perform a complete sterilization of the water within the pool before the pool can be re-opened again for use.

Accordingly, there is a need for a diaper having a specific construction which prevents human waste from leaking out of the diaper through holes designed to receive a user's legs therethrough.

There is also a need for a diaper that has a specific enhanced material formed around holes designed for a user's legs to fit therethrough, where such enhanced material will conform around the legs inserted through the holes.

Summary of the Inventive Concept

The present general inventive concept provides reusable swim diapers which can provide a snug fit. More particularly, but not exclusively, the inventive concept provides reusable swim diapers including specifically designed gussets with an elastic and enhanced material configured to provide a snug fit and to prevent leakage accidents of human waste in pools or other bathing facilities.

Additional features and utilities of the present general inventive concept will be set forth in part in the description which follows and, in part, will be obvious from the description, or may be learned by practice of the general inventive concept.

The foregoing and/or other features and utilities of the present general inventive concept may be achieved by providing a reusable swim diaper, comprising: a main body having a circular elastic waist opening configured to fit around a waist of a user and two circular elastic leg insertion openings each to receive therethrough a respective leg of a user, one side of the main body being configured to open and close by at least two sets of snaps vertically attached thereto such that when the sets of snaps are open the circular elastic waist opening is broken and one of the two circular leg insertion openings is broken and when the at least two sets of snaps are closed the circular elastic waist opening is formed and one of the two circular elastic leg insertion openings is formed; and a gusset sewn to a lower half of an inner circumferential section of each elastic leg insertion hole to form an enhanced contact with the leg of a user to block particulate matter from leaking from inside the diaper to outside the diaper.

In an exemplary embodiment, each gusset can be sewn to the lower half of the inner circumferential section of the respective leg insertion hole from approximately the three o'clock position to approximately the nine o'clock position of the elastic insertion hole, thus forming a pocket-like section extending from the lower half of the corresponding elastic leg insertion hole.

In another exemplary embodiment, the main body can be formed of a waterproof coated bonded polyurethane knitted polyester material.

In another exemplary embodiment, each gusset can be formed of a waterproof coated bonded polyurethane knitted polyester material.

In still another exemplary embodiment, the circumferential elastic waist opening includes an elastic waist seam to elastically surround the waist of a user and provide a secure fit with the waist of the user.

In still another exemplary embodiment, the elastic waist seam includes an elastic material sewn to the inside of the waist region to form a comfort seam around the circumferential elastic waist opening.

In yet another exemplary embodiment, the at least two sets of snaps attached vertically include four snaps attached vertically.

The foregoing and/or other features and utilities of the present general inventive concept may also be achieved by providing a swim diaper, comprising: a main body formed of a waterproof coated bonded polyurethane knitted polyester material and including: first and second ends and an elastic waist seam extending along the length of the main body from the upper first end to the upper second end and an elastic leg seam extending along the length of the main body from the lower first end to the lower second end; a first circular elastic leg opening with an elastic leg seam to receive one leg of a user therethrough; at least two snaps attached at each of the first and second ends such that when the snaps at the first end are snapped to the snaps at the second end a circular elastic waist opening is formed and a second circular elastic leg opening with an elastic seam is formed to receive another leg of a user therethrough; and a gusset sewn to a lower half of an inner circumferential section of the first elastic leg seam and between two sections of the elastic leg seam such that when the at least two snaps are snapped together each gusset forms an enhanced contact with the respective leg of a user to block particulate matter from leaking from inside the diaper to outside the diaper.

In an exemplary embodiment, each gusset is formed of a waterproof coated bonded polyurethane knitted polyester material.

In another exemplary embodiment, the at least two sets of snaps include four sets of snaps attached vertically along the first and second ends of the main body.

In another exemplary embodiment, when the four sets of snaps are snapped together each gusset extends along the lower half of an inner circumferential section of the respective elastic leg opening and seam from approximately the three o'clock position to approximately the nine o'clock position of the elastic leg opening and seam, thus forming a pocket-like section extending from the lower half of the corresponding elastic leg opening and seam.

In still another exemplary embodiment, the elastic waist seam includes an elastic material sewn along the inside portion thereof to form a comfort seam along the length thereof.

BRIEF DESCRIPTION OF THE DRAWINGS

These and/or other features and utilities of the present inventive concept will become apparent and more readily appreciated from the following description of the embodiments, taken in conjunction with the accompanying drawings of which.

Figure 1:
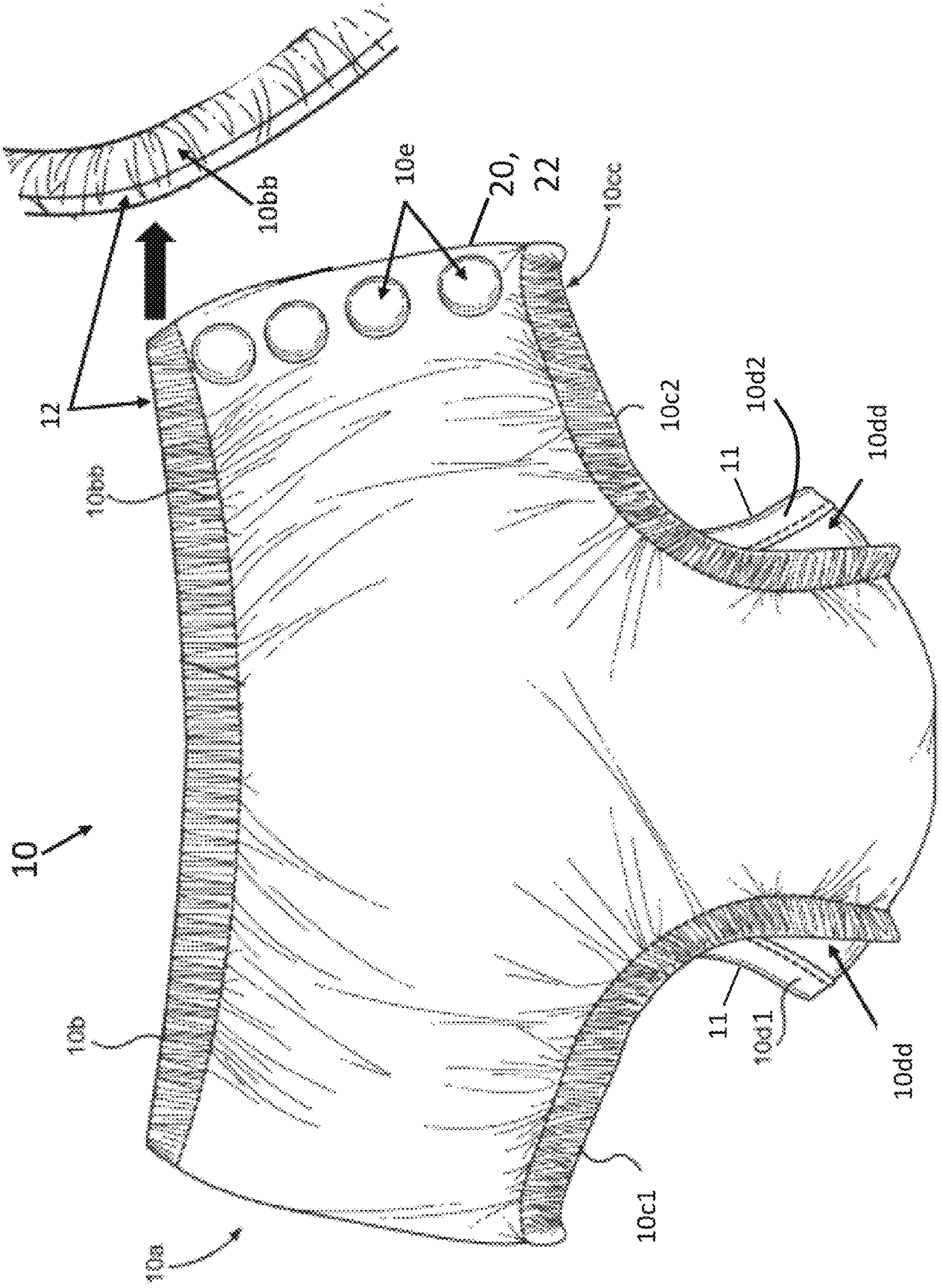
FIG. 1 illustrates a front plan view of a diaper including gussets, according to an example embodiment of the present inventive concept.

The drawings illustrate a few example embodiments of the present inventive concept, and are not to be considered limiting in scope, as the overall inventive concept may admit to other equally effective embodiments. The elements and features shown in the drawings are to scale and attempt to clearly illustrate the principles of exemplary embodiments of the present inventive concept. In the drawings, reference numerals designate like or corresponding, but not necessarily identical, elements throughout the several views.

DETAILED DESCRIPTION OF THE PREFERRED EMBODIMENTS

Reference will now be made in detail to the embodiments of the present general inventive concept, examples of which are illustrated in the accompanying drawings, wherein like reference numerals refer to the like elements throughout. The embodiments are described below in order to explain the present general inventive concept while referring to the figures. Also, while describing the present general inventive concept, detailed descriptions about related well-known functions or configurations that may diminish the clarity of the points of the present general inventive concept are omitted.

It will be understood that although the terms "first" and "second" are used herein to describe various elements, these elements should not be limited by these terms. These terms are only used to distinguish one element from another element. Thus, a first element could be termed a second element, and similarly, a second element may be termed a first element without departing from the teachings of this disclosure.

Expressions such as "at least one of," when preceding a list of elements, modify the entire list of elements and do not modify the individual elements of the list.

All terms including descriptive or technical terms which are used herein should be construed as having meanings that are obvious to one of ordinary skill in the art. However, the terms may have different meanings according to an intention of the applicant, case precedents, or the appearance of new technologies. Also, some terms may be arbitrarily selected by the applicant, and in this case, the meaning of the selected terms will be described in detail in the detailed description of the invention provided herein. Thus, the terms used herein have to be defined based on the meaning of the terms together with the description throughout the specification.

Hereinafter, one or more exemplary embodiments of the present general inventive concept will be described in detail with reference to accompanying drawings.

Example embodiments of the present general inventive concept are directed to reusable swim diapers having specifically designed gussets with an elastic and enhanced material configured to provide a snug fit and to prevent leakage accidents of human waste in pools.

FIG. 1 illustrates a front plan view of a diaper 10 including specifically designed gussets, according to an example embodiment of the present inventive concept. Referring to FIG. 1, this diaper 10 includes a one-piece main body **10*a* formed of a waterproof coated bonded polyurethane knitted polyester material. More specifically, this waterproof coated bonded polyurethane knitted polyester material is a composite material made of one or more layers of polymer resins joined by urethane links and a knitted polyester backing. This material provides improved durability and performance for use as a reusable swim diaper 10**, as described in more detail below. Further, this material has an increased resistance to degradation due to laundering, which occurs with conventional diapers, and is suitable for multiple launderings and reuse with minimal degradation.

The one-piece main body **10*a* is configured to include a circular waist region 10*b* to surround a user's waist and a pair of circular elastic leg insertion holes 10*c*1, 10*c*2** to receive a respective leg of a user.

The waist region **10*b* can include an elastic waist seam 10*bb* to elastically surround the waist of a user and provide a secure fit. The waist seam 10*bb* can be formed by sewing an elastic material to the inside of the waist region 10*b* such that a comfort seam 12 is provided. The comfort seam 12 can be formed by turning both edges of the outer and inner waist region 10*b*** material inside and sewing them together so rough end edges of the material are concealed within the seam and not exposed, thus eliminating any edges that would otherwise rub against the waist of the user.

The circular elastic leg insertion holes 10$c$1,10$c$2 can also include an elastic leg insertion hole seam 10$cc$ to elastically surround the leg of a user and provide a secure fit. The elastic leg insertion hole seam 10$cc$ can be formed in the same manner as the waist seam 10$bb$ with comfort seams (not illustrated) formed by turning both inner and outer edges of the leg opening material inside and sewing them together so rough end edges of the material are concealed within the seam and not exposed, thus eliminating any edges that would otherwise rub against the leg of the user.

Figure 2:
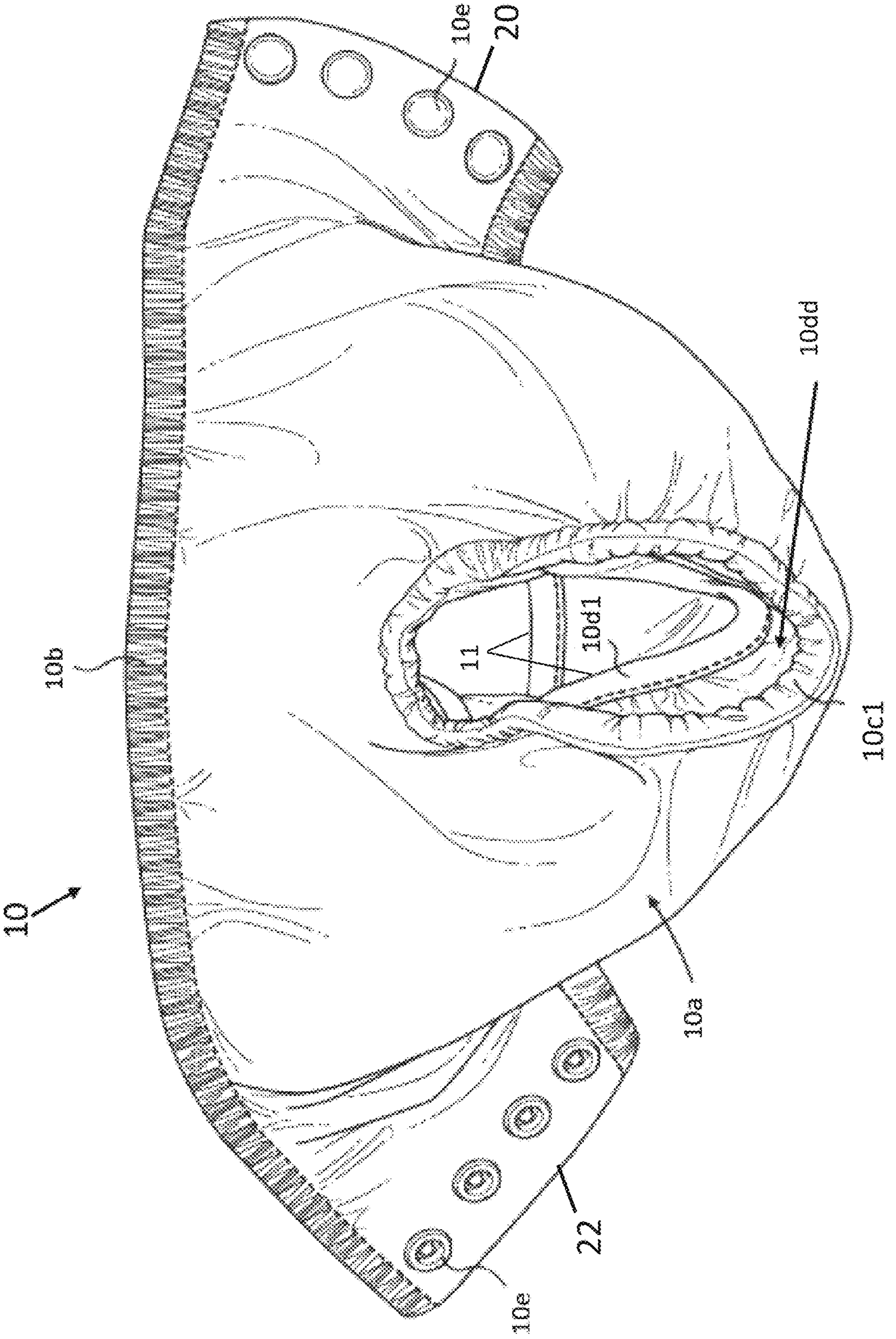
FIG. 2 illustrates a perspective view of a first side of the diaper according to the example embodiment of FIG. 1, showing a first leg hole and gusset combination.

FIG. 2 illustrates a perspective view of a first side of the diaper 10 according to the example embodiment of FIG. 1, showing a first leg insertion hole 10$c$1 and a gusset 10$d$1 combination. Referring to FIGS. 1 and 2, the elastic leg insertion holes 10$c$1, 10$c$2 are configured to have a predetermined circumferential diameter to receive a user's leg therein. It is to be noted that the size of the diaper 10, the circumference of the waist region 10$b$ and the circumference of the leg insertion holes 10$c$1, 10$c$2 can be varied for different size users to fit therein.

According to an example embodiment of the present inventive concept, a gusset 10$d$1, 10$d$2 can be sewn around a lower and inner circumferential section of each of the respective elastic leg insertion hole 10$c$1, 10$c$2 with a free edge 11 spaced away from the lower and inner circumferential section of the corresponding elastic leg insertion hole 10$c$1, 10$c$2. More specifically, the gusset 10$d$1, 10$d$2 can be sewn to the inner circumferential section of an each elastic insertion hole 10$c$1, 10$c$2 from approximately the three o'clock position to approximately the nine o'clock position of the elastic insertion hole 10$c$1, 10$c$2, thus forming a pocket-like section 10$dd$ extending from the lower half of the elastic leg insertion hole 10$c$1, 10$c$2. The gusset 10$d$1, 10$d$2 can be formed of the same waterproof coated (bonded polyurethane) knitted polyester material as the main body 10$a$. The gussets 10$d$1, 10$d$2 can be made in the same manner as the comfort seam 12 of the waist seam 10$bb$, with rough edges turned inside and sewn together so that no rough edges are exposed. The gussets 10$d$1, 10$d$2, including the pocket-like section 10$dd$, are configured to enable a snug fit and to add protection against pool accidents, such as leakage of feces out of the elastic leg insertion holes 10$c$1, 10$c$2.

The exterior surface of the polyester material of the diaper 10 may be printed with ornamental and decorative features. The interior surface of the polyester material of the diaper 10 desirably has an absorbent material 14, such as terrycloth, bonded thereto. The absorbent material 14 can be two layers of terrycloth provided as by a polyester/polyamide fiber blend. However, the absorbent material 14 can be formed of other equivalent materials which will provide the intended purpose of retaining fecal matter, without departing from the spirit and scope of the present inventive concept.

Figure 3:
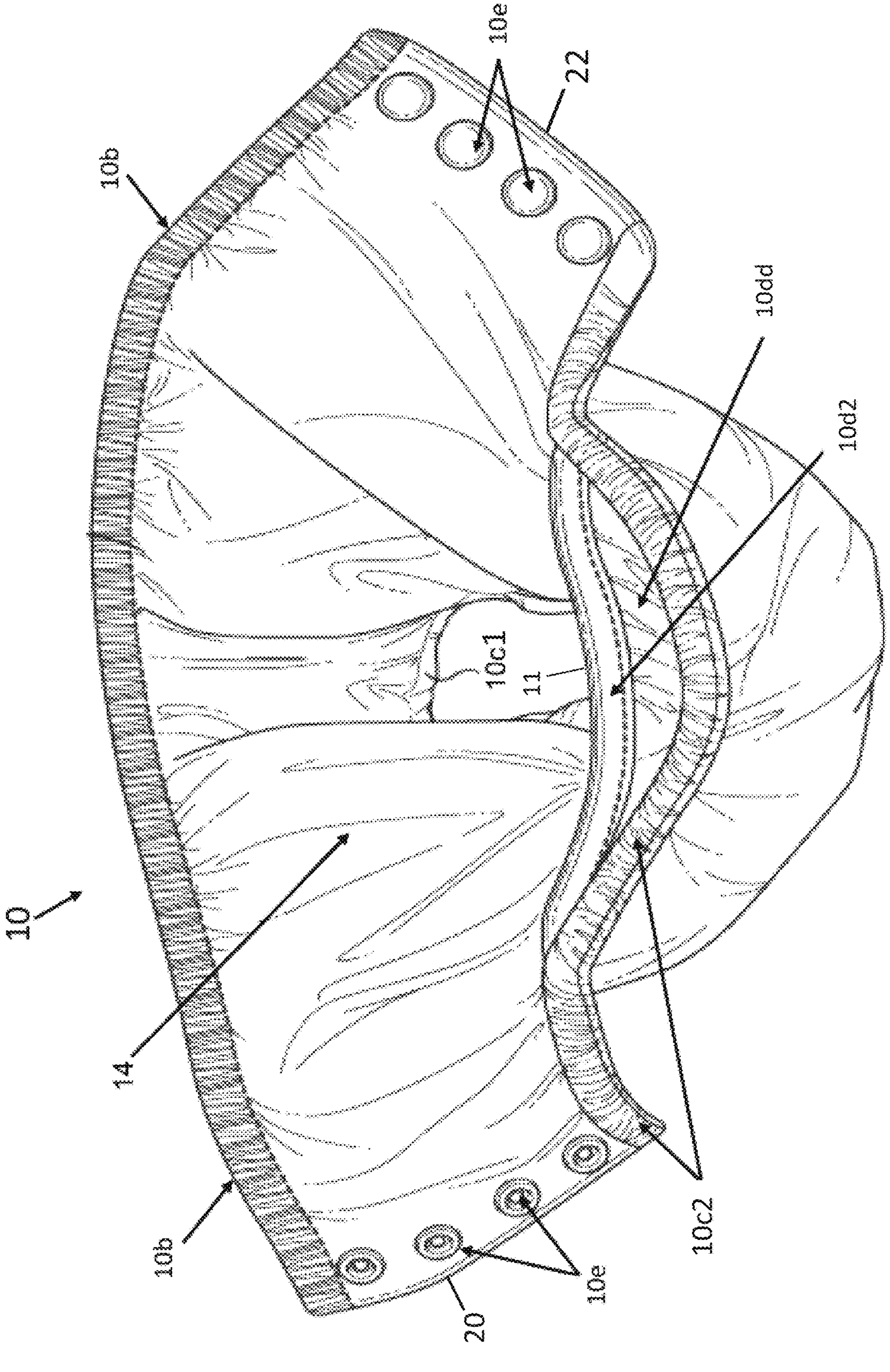
FIG. 3 illustrates an internal and perspective view of a second side of the diaper in an open position, according to the example embodiment of FIG. 1.
Figure 4:
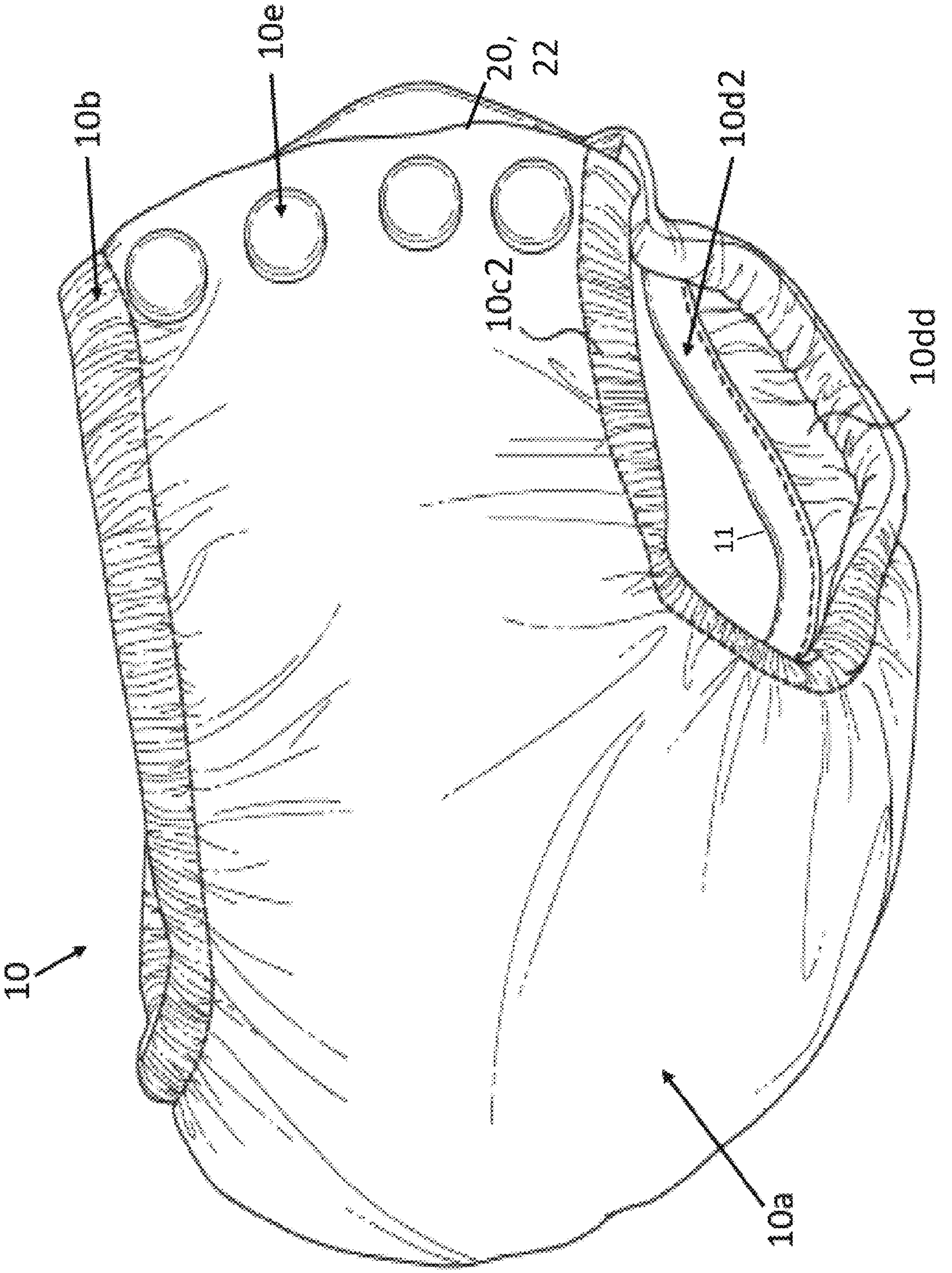
FIG. 4 illustrates a perspective view of the second side of the diaper in a closed position, according to the example embodiment of FIG. 1, showing a second leg hole and gusset combination.

FIG. 3 illustrates an internal and open perspective view of a second side of the diaper according to the example embodiment of FIG. 1, and FIG. 4 illustrates a closed perspective view of the second side of the diaper according to the example embodiment of FIG. 1, showing the second leg hole 10$c$2 and gusset combination 10$d$2. Referring to FIG. 3, one side of the swim diaper 10 can be separated into two sections, wherein first and second ends 20,22 of each of the two sections includes at least two snaps 10$e$. In this example embodiment each of the two sections include four snaps. Referring to FIG. 4, when the two separated sections are brought together they can be snapped together to form the second one of the two elastic leg insertion holes 10$c$2. It is to be noted that alternative equivalent ways of closing the two sections of the swim diaper 10 together can be used, such as, for example Velcro® or buttons, without departing from the spirit and scope of the overall present inventive concept.

The construction of the diaper 10, including the materials utilized, the elastic apertures at the waist and leg openings, and the additional gussets 10$d$1, 10$d$2, serve to minimize or eliminate the flow of particulate matter, such as fecal matter, between the inside and the outside of the swim diaper 10. In particular, the gussets 10$d$1, 10$d$2 provide an enhanced protection against particulate matter, such as fecal matter, from leaking out between the elastic leg insertion holes 10$c$1, 10$c$2 and the respective user's leg, which is inserted therethrough.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

What is claimed is:

1. A reusable swim diaper, comprising:

a main body including a circular elastic waist opening configured to fit around a waist of a user and two circular elastic leg insertion holes each to receive therethrough a respective leg of a user, one side of the main body being configured to open and close by at least two sets of snaps vertically attached thereto such that when the sets of snaps are open the circular elastic waist opening is broken and one of the two circular leg insertion holes is broken and when the at least two sets of snaps are closed the circular elastic waist opening is formed and one of the two circular elastic leg insertion holes is formed; and a gusset sewn to a lower half of an inner circumferential section of each elastic leg insertion hole from approximately a three o'clock position to approximately a nine o'clock position relative to the elastic leg insertion hole with the elastic leg insertion hole being vertically below the circular elastic waist opening, the gusset forming a pocket with a free edge spaced away from the lower half of the inner circumferential section of the corresponding elastic leg insertion hole, the gusset and the pocket forming an enhanced contact with the leg of a user to block particulate matter from leaking from inside the diaper to outside the diaper.

2. The reusable swim diaper according to claim 1, wherein the main body is formed of a waterproof coated bonded polyurethane knitted polyester material.

3. The reusable swim diaper according to claim 2, wherein each gusset is formed of a waterproof coated bonded polyurethane knitted polyester material.

4. The reusable swim diaper according to claim 1, wherein the circumferential elastic waist opening includes an elastic waist seam to elastically surround the waist of a user and provide a secure fit with the waist of the user.

5. The reusable swim diaper according to claim 4, wherein the elastic waist seam includes an elastic material sewn to an inside of a waist region to form a comfort seam around the circular elastic waist opening.

6. The reusable swim diaper according to claim 1, wherein the at least two sets of snaps attached vertically include four snaps attached vertically.

7. A swim diaper, comprising:

a main body formed of a waterproof coated bonded polyurethane knitted polyester material, the main body including first and second ends;

an elastic waist seam extending along a circumference of a waist region of the main body from the first end to the second end;

a first circular elastic leg opening with a first elastic leg seam to receive one leg of a user therethrough;

a second elastic leg seam extending along the main body from the first end to the second end;

at least two snaps attached at each of the first and second ends such that when the snaps at the first end are snapped to the snaps at the second end, a circular elastic waist opening is formed and a second circular elastic leg opening is formed from the second elastic leg seam to receive another leg of a user therethrough;

a first gusset sewn to a lower half of an inner circumferential section of the first circular elastic leg opening and extending from approximately a three o'clock position to approximately a nine o'clock position relative to the first circular elastic leg opening with the first circular elastic leg opening being vertically below the elastic waist seam, the first gusset forming a pocket with a free edge spaced away from the lower half of the inner circumferential section of the first circular elastic leg opening, the first gusset and the pocket of the first gusset forming an enhanced contact with the respective leg of the user to block particulate matter from leaking from inside the diaper to outside the diaper; and a second gusset sewn between two sections of the elastic leg seam such that when the at least two snaps are snapped together, the second gusset extends from a lower half of an inner circumferential section of the second circular elastic leg opening from approximately a three o'clock position to approximately a nine o'clock position relative to the second circular elastic leg opening with the second circular elastic leg opening being vertically below the elastic waist seam, the second gusset forming a pocket with a free edge spaced away from the lower half of the inner circumferential section of the second circular elastic leg opening, the second gusset and the pocket of the second gusset forming an enhanced contact with the respective leg of the user to block particulate matter from leaking from inside the diaper to outside the diaper.

8. The swim diaper according to claim 7, wherein each gusset is formed of a waterproof coated bonded polyurethane knitted polyester material.

9. The swim diaper according to claim 7, wherein the at least two sets of snaps include four sets of snaps attached vertically along the first and second ends of the main body.

10. The swim diaper according to claim 7, wherein the elastic waist seam includes an elastic material sewn along the inside portion thereof to form a comfort seam along the length thereof.

* * * * *